United States Patent [19]

Gerlitz et al.

[11] Patent Number: 5,453,373
[45] Date of Patent: Sep. 26, 1995

[54] PROTEIN C DERIVATIVES

[75] Inventors: Bruce E. Gerlitz; Brian W. Grinnell, both of Indianapolis, Ind.

[73] Assignee: Eli Lilly and Company, Indianapolis, Ind.

[21] Appl. No.: 89,215

[22] Filed: Jul. 9, 1993

Related U.S. Application Data

[63] Continuation of Ser. No. 887,191, May 21, 1992, abandoned.

[51] Int. Cl.$^6$ .............................. C12N 5/00; C12N 15/00; C12P 21/06; C07H 19/00
[52] U.S. Cl. ............................ 435/240.2; 424/94.64; 435/69.1; 435/212; 435/252.33; 435/320.1; 514/2; 536/22.1; 536/23.1; 536/23.2; 536/23.4
[58] Field of Search .................... 424/94, 64; 435/69.1, 435/212, 240.2, 252.33, 320.1; 514/2; 536/22.1, 23.1, 23.2, 23.4

[56] References Cited

U.S. PATENT DOCUMENTS

| | | | |
|---|---|---|---|
| 4,775,624 | 10/1988 | Bang et al. | 435/226 |
| 4,981,952 | 1/1991 | Yan | 530/384 |
| 4,992,373 | 2/1991 | Bang et al. | 435/226 |

FOREIGN PATENT DOCUMENTS

| | | |
|---|---|---|
| 0323149 | 7/1989 | European Pat. Off. . |
| 0443874 | 8/1991 | European Pat. Off. . |

OTHER PUBLICATIONS

U.S. Patent Application Ser. No. 07/771,880 filed Oct. 4, 1991 by Bang et al.
U.S. Patent Application Ser. No. 07/484,133 filed Feb. 23, 1990 by Gerlitz et al.
U.S. Patent Application Ser No. 07/628,063 filed Dec. 21, 1990 by Gerlitz et al.
Ehrlich, et. al., 1990, *EMBO J.* 9:2367–2373.
Grinnell, et. al., 1991, *J. Biol. Chem.* 226:9778–9785.
Grinnell, et. al., in *Protein C and Related Anticoagulants* (eds. Bruley, D & Drohan, W.) 29–63 (Gulf Publishing Co., Houston, 1990).
Grinnell et. al., 1987, *Bio/Technology* 5:1189–1192.
LeBonniec, et. al., 1991, *Proc. Natl. Acad. Sci. USA* 88:7371–7375.
LeBonniec, et. al., 1991, *J. Biol. Chem.* 266:13796–13803.

*Primary Examiner*—Charles L. Patterson, Jr.
*Assistant Examiner*—Hyosuk Kim
*Attorney, Agent, or Firm*—Douglas K. Norman; John C. Demeter; David E. Boone

[57] ABSTRACT

Human protein C derivatives with high activity and reduced dependence on thrombin activation are described. These derivatives differ from the native forms of human protein C in their increased activation rates, functional activities and carbohydrate structures. DNA compounds, transfer vectors, expression vectors and transformants useful in producing these derivatives are also described.

28 Claims, No Drawings

PROTEIN C DERIVATIVES

This application is a continuation of application Ser. No. 07/887,191, filed May 21, 1992, now abandoned.

FIELD OF THE INVENTION

The present invention is in the field of human medicine, particularly in the treatment of blood coagulation disorders. Most specifically, the invention relates to derivatives of the human protein C molecule, methods of using these derivatives and pharmaceutical compositions comprising these protein C derivatives.

BACKGROUND OF THE INVENTION

Protein C is a vitamin K dependent plasma protein which circulates mainly as an inactive disulfide-linked heterodimer consisting of a light chain of about 25 kilodaltons and a heavy chain of about 41 kilodaltons. The heavy chain contains the serine protease domain with its N-terminal activation peptide while the light chain contains the region of gamma-carboxyglutamic acid residues that is required for calcium-dependent membrane binding and functional activity. The inactive human protein C zymogen is converted into activated protein C by the action of the thrombin/thrombomodulin complex which cleaves the activation peptide (residues 158 through 169 of the circulating zymogen or residues 200 through 211 of the preprozymogen) to form activated protein C.

The role of protein C as a therapeutic agent is well recognized (see, for example, Bang et.al., U.S. Pat. No. 4,775,624 which discloses the DNA sequence encoding human protein C zymogen and Bang et.al., U.S. Pat. No. 4,992,373 which discloses a method for producing activated human protein C). A human protein C derivative designated FLIN was disclosed by Gerlitz et.al. in European Patent Application Serial No. 91301450.2. This FLIN derivative contains a Phe residue rather than an Asp residue at position 167 of the Activation Peptide (position 206 of the preprozymogen) and an Asn residue rather than an Asp residue at position 172 within the Heavy Chain (position 214 of the preprozymogen). The FLIN derivative is more readily activated by thrombin than is the wild type human protein C zymogen. Other human protein C derivatives, designated Q313 and Q329, were disclosed by Gerlitz et.al. in European Patent Application Serial No. 91301446.0. The Q313 derivative contains a Gln residue rather than an Asn residue at position 313 of the wild type zymogen while the Q329 derivative contains a Gln residue rather than an Asn residue at position 329 of the wild type zymogen. These Q313 and Q329 derivatives lack the carbohydrate structures normally associated with the Asn residue at these sites on the wild type molecule and therefore display increased amidolytic and functional activities.

SUMMARY OF THE INVENTION

The present invention relates to derivatives of human protein C modified by changing amino acid 313 of the native human protein C molecule from asparagine to glutamine and by changing amino acid 167 of the native human protein C molecule from aspartic acid to phenylalanine and by changing amino acid 172 of the native human protein C molecule from aspartic acid to asparagine. These molecules may also be modified at position 329 of the native human protein C molecule by changing the wild type asparagine residue to a glutamine residue. The change in residue 329 may be made only in conjunction with the change in residue 313 or it may also be made in conjunction with the changes in residues 167 and 172. Said human protein C derivatives are more readily activated by thrombin and are also more functionally active than the wild type human protein C molecule or any other human protein C derivative.

Also disclosed and claimed are recombinant DNA constructions, vectors and transformants useful in producing the novel human protein C derivatives. Further, pharmaceutical compositions containing an effective amount of a human protein C derivative of the invention in combination with one or more pharmaceutically acceptable excipients are disclosed and claimed, as well as methods of using the derivatives in the treatment and prevention of disease states.

For purposes of the present invention, as disclosed and claimed herein, the following terms and abbreviations are as defined below.

Q313—a human protein C derivative wherein the asparagine residue at position 313 of the native human protein C molecule has been changed to a glutamine residue.

Q329—a human protein C derivative wherein the asparagine residue at position 329 of the native human protein C molecule has been changed to a glutamine residue. Protein C derivatives Q313 and Q329 are disclosed in Gerlitz et.al., U.S. patent application Ser. No. 07/628,063; Gerlitz et.al., European Patent Application Serial No. 91301446.0 and Grinnell et.al., 1991, *J. Biol. Chem*, 226:9778–9785, the teachings of which are herein incorporated by reference.

Q3Q9—a human protein C derivative wherein the asparagine residue at position 313 of the native human protein C molecule has been changed to a glutamine and the asparagine residue at position 329 of the native human protein C molecule has been changed to glutamine residue.

F167—a human protein C derivative wherein the aspartic acid residue at position 167 of the native human protein C molecule has been changed to a phenylalanine. Protein C derivative F167 is disclosed in Bang et.al., U.S. patent application Ser. No. 07/771,880; Bang et.al. European Patent Application Serial No. 88312201.2 and Ehrlich et.al., 1990, *EMBO J.* 9:2367–2373, the teachings of which are herein incorporated by reference.

LIN—a human protein C derivative wherein the aspartic acid residue at position 172 of the native human protein C molecule has been changed to an asparagine residue.

FLIN—a human protein C derivative wherein the aspartic acid residue at position 167 of the native human protein C molecule has been changed to a phenylalanine and the aspartic acid residue at position 172 of the native protein C molecule has been changed to a asparagine residue. Protein C derivatives LIN and FLIN are disclosed in Gerlitz et.al., U.S. patent application Ser. No. 07/484,133; Gerlitz et.al., European Patent Application Serial No. 91301450.2, and Grinnell et.al., in *Protein C and Related Anticoagulants* (eds. Bruley, D. & Drohan, W.) 13–46 (Gulf Publishing Co., Houston, 1990), the teachings of which are herein incorporated by reference.

FLIN-Q313—a human protein C derivative wherein the aspartic acid residue at position 167 of the native human protein C molecule has been changed to a phenylalanine, the aspartic acid residue at position 172 of the native protein C molecule has been changed to a asparagine residue and the asparagine residue at position 313 of the native protein C molecule has been changed to a glutamine residue.

FLIN-Q3Q9—a human protein C derivative wherein the aspartic acid residue at position 167 of the native human protein C molecule has been changed to a phenylalanine, the aspartic acid residue at position 172 of the native protein C molecule has been changed to a asparagine residue, the asparagine residue at position 313 of the native protein C molecule has been changed to a glutamine residue and the asparagine residue at position 329 of the native protein C molecule has been changed to a glutamine residue.

GBMT transcription unit—a modified transcription control unit comprising the P2 enhancer of BK virus spaced closely to the upstream regulatory element of the adenovirus major late promoter (MLTF), the adenovirus-2 major late promoter, a poly GT element positioned to stimulate said promoter and a DNA sequence containing the spliced tripartitie leader sequence of adenovirus.

Nascent protein—the polypeptide produced upon translation of an mRNA transcript, prior to any post-translational modifications. However, post-translational modifications such as gamma-carboxylation of glutamic acid residues and hydroxylation of aspartic acid residues may begin to occur before a protein is fully translated from an mRNA transcript.

Protein C Activity—any property of human protein C responsible for proteolytic, amidolytic, esterolytic, and biological (anticoagulant or profibrinolytic) activities. Methods for testing for protein anticoagulant activity are well known in the art, i.e., see Grinnell et.al., 1987, Bio/Technology 5:1189–1192.

Zymogen—an enzymatically inactive precursor of a proteolytic enzyme. Protein C zymogen, as used herein, refers to secreted, inactive forms, whether one chain or two chain, of protein C.

All amino acid abbreviations used in this disclosure are those accepted by the United States Patent and Trademark Office as set forth in 37 C.F.R. §1.822(b)(2) (1990).

DETAILED DESCRIPTION OF THE INVENTION

The present invention provides human protein C derivatives which have altered glycosylation patterns and also which have altered activation regions. Specifically, these derivatives include Q3Q9, FLIN-Q313 and FLIN-Q3Q9. Derivative Q3Q9 contains glutamine residues at positions 313 and 329 of the protein C molecule (rather than the asparagine residues normally found in these positions). Derivative FLIN-Q313 contains a phenylalanine residue at position 167 of the molecule and an asparagine residue at position 172 of the molecule (rather than the aspartic acid residues normally found in these positions) as well as a glutamine residue at position 313 (rather than the asparagine residue normally found in this position). In derivative FLIN-Q3Q9, the residue at position 167 has been changed from an aspartic acid to a phenylalanine, the residue at position 172 has been changed from an aspartic acid to an asparagine, the residue at position 313 has been changed from asparagine to glutamine and the residue at position 329 has been changed from asparagine to glutamine.

Derivatives FLIN-Q313 and FLIN-Q3Q9 demonstrate exceptionally high rates of activation by thrombin alone. Furthermore, both derivative FLIN-Q313 and FLIN-Q3Q9, unlike wild type human protein C, can be activated by thrombin generated in clotting human plasma, resulting in an inhibition of further clot formation. This clot-activated pro-enzyme has a substantially greater specific activity and longer half-life than the activated form of natural protein C. The derivatives of the present invention therefore can be used as site-activated anti-thrombotic agents, having no anti-coagulant activity except in the presence of significant thrombin generation.

The invention also provides DNA compounds for use in making the protein C derivatives. These DNA compounds comprise the coding sequence for the light chain of human protein C positioned immediately adjacent to, downstream of, and in translational reading frame with the prepropeptide sequence of wild-type zymogen protein C. The DNA sequences also encode the Lys-Arg dipeptide which is processed during maturation of the protein C molecule, the activation peptide and the heavy chain of the protein C molecule. The changes in the amino acid residues at positions 167 172 and 313 alter the activation of the molecule while the changes in the amino acid residues at postions 313 and 329 alter the carbohydrate content of the molecule.

Those skilled in the art will recognize that, due to the degeneracy of the genetic code, a variety of DNA compounds can encode the polypeptides described above. Bang et.al., U.S. Pat. No. 4,775,624, the entire teaching of which is herein incorporated by reference, discloses and claims the DNA sequence encoding the wild-type form of the human protein C molecule. In that the skilled artisan could readily determine which changes in the DNA sequences might be used to construct the other DNA sequences which could encode the exact polypeptides as disclosed herein, the invention is not limited to the specific DNA sequences disclosed by deposit. Consequently, the constructions described below and in the accompanying Examples for the preferred DNA compounds, vectors and transformants of the invention are merely illustrative and do not limit the scope of the invention. In addition, the substitution of Gln in place of Asn at positions 313 and 329 is illustrative and does not limit the scope of the invention as other substitutions, with the exception of Cys or Pro, could be used.

All of the DNA compounds of the present invention were prepared by site-directed mutagenesis of the human protein C gene. The mutagenized zymogen encoding molecules were then inserted into eukaryotic expression vectors such that expression of the zymogen genes can be driven by the GBMT transcription unit. These vectors were transformed into *Escherichia coli* K12 AG1 cells and deposited and made part of the permanent stock culture collection of the Northern Regional Research Laboratories in Peoria, Ill. 61604 on Jan. 14, 1992. The specific cultures and accession numbers are found in Table I.

TABLE I

| Culture | Accession Number |
| --- | --- |
| *E. coli* K12 AG1/pGT-h-Q3Q9 | NRRL B-18938 |
| *E. coli* K12 AG1/pGT-h-FLIN-Q313 | NRRL 3-18939 |
| *E. coli* K12 AG1/pGT-h-FLIN-Q3Q9 | NRRL B-18940 |

The cultures are obtained and the plasmids are isolated using conventional techniques, and then may be directly transfected into eukaryotic host cells for the production of the derivatives of human protein C. It is preferable to transfect the plasmids into host cells which express the adenovirus E1A immediate-early gene product, in that the BK enhancer found in the GBMT transcription control unit functions to enhance expression most efficiently in the presence of E1A. The GBMT transcription control unit is more fully described in Berg et.al., U.S. patent application Ser. No. 07/484,082 and Berg et.al., European Patent Application Serial No. 91301451.0, the entire teachings of which are herein incorporated by reference. Skilled artisans realize that a number of host cells express, or can be made to express, an immediate early gene product of a large DNA virus. The most preferred cell line for expression on the human protein C derivatives of the present invention is the human kidney 293 cell line which is disclosed in Bang et.al., U.S. Pat. No. 4,992,373, the entire teaching of which is herein incorporated by reference. After expression in the cell line, the derivatives are purified from the cell culture supernatent using the prodedure of Yan, U.S. Pat. No. 4,981,952, the entire teaching of which is herein incorporated by reference.

The DNA sequences of the invention can be synthesized chemically, or by combining restriction fragments, or by a combination of techniques known in the art. DNA synthesizing machines are available and can be used to contruct the DNA compounds of the present invention.

The illustrative vectors of the invention comprise the GBMT transcription unit positioned to stimulate transcription of the coding sequences by the adenovirus late promoter. Those skilled in the art recognize that a great number of eukaryotic promoters, enhancers, and expression vectors are known in the art and can be used to express the DNA sequences to produce the protein C derivatives of the present invention. Those skilled in the art also recognize that a eukaryotic expression vector can function without an enhancer element. The key aspect of the present invention does not reside in the particular enhancer or promoter used to express the derivatives, but rather with the novel DNA sequences and correponding proteins made from those sequences.

The vectors of the present invention can be transformed into and expressed in a wide variety of eukaryotic, especially mammalian, host cells. The vectors deposited at the NRRL all contain the hygromycin resistance conferring gene. However, vectors which contain no selectable marker can easily be constructed and can be used to perform transient assays or can be cotransformed into cell lines along with other vectors which contain selectable markers. The vectors of the invention can also comprise sequences that allow for replication in *E. coli*, as it is usually more efficient to prepare plasmid DNA in *E. coli* rather than in other host organisms.

Many modifications and variations of the present illustrative DNA sequences and plasmids are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence of human protein C and can be constructed by following conventional synthetic or site-directed mutagenesis procedures. Synthetic methods can be carried out in substantial accordance with the procedures of Itakura et.al., 1977 *Science* 198:1056 and Crea et.al., 1978, *Proc. Natl. Acad. Sci, USA* 75:5765. Therefore, the present invention is in no way limited to the DNA sequences and plasmids specifically exemplified.

Methods for the activation of zymogen forms of human protein C to activated human protein C derivatives are old and well known in the art. Protein C may be activated by thrombin alone, by a thrombin/thrombomodulin complex, by Russell's Viper venom or by a variety of other means. The activity of human protein C derivatives may be measured following thrombin activation by either total amidolytic assays or by anticoagulation assays. Thrombin activation and protein C assays (amidolytic and anticoagulant) were performed according to the teaching of Grinnell et.al., 1987, *Bio/Technology* 5:1187–1192, the entire teaching of which is herein incorporated by reference.

The recombinant human protein C derivatives of the present invention are useful in the prevention and treatment of a wide variety of acquired disease states involving intravascular coagulation, including deep vein thrombosis, pulmonary embolism, pereipheral arterial thrombosis, emboli originating from the heart or peripheral arteries, acute mycardial infarction, thrombotic strokes, unstable angina, peripheral vascular surgery, organ transplantaion and disseminated intravascular coagulation. These protein C derivatives can also be used efficiently in the treatment of the significant numbers of patients with heterozygous protein C deficiencies presenting recurrent deep vein thrombosis and in the case of the homozygous protein C deficient patients with purpura fulminans. Yet another therapeutic indication of activated protein C derivatives is the prevention of deep vein thrombosis and pulmonary embolism currently treated with low doses of heparin.

The derivatives, and activated counterparts, of the present invention can be formulated according to known methods to prepare pharmaceutically useful compositions, whereby a human protein C derivative or activated protein C derivative of the present invention is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences* 16th ed., 1980, Mack Publishing Co., edited by Osol et.al., which is herein incorporated by reference. Such compositions will contain an effective amount of a protein C derivative, or activated counterpart, together with a suitable amount of carrier vehicle to prepare pharmaceutically acceptable compositions suitable for effective administration to the host. The protein C derivative composition can be administered parenterally, or by other methods tha ensure delivery to the bloodstream in effective form.

The following examples are provided as a means of illustrating the present invention and are not to be construed as a limitation thereon.

EXAMPLE 1

Production of Human Protein C Derivatives

The expression vectors of the present invention are isolated from *E. coli* cells then tranformed into 293 cells, transformants were selected at 37° C., then cultured to produce the human protein C derivatives, in substantial accordance with the teachings of Bang et.al., U.S. Pat. No. 4,992,373, which is incorporated herein by reference. The derivatives are purified out of the cell culture supernatent in substantial accordance with the teachings of Yan, U.S. Pat. No. 4,981,952, which is incorporated herein by reference.

EXAMPLE 2

Anticoagulant Activities

Fully activated protein C was obtained by activating material with 10 nM thrombin in complex with soluble recombinant human thrombomodulin TMD-75 as described by Parkinson et.al., 1990, *J. Biol. Chem.* 265:12602–12610, the teaching of which is herein incorporated by reference. The anticoagulant activity of the activated molecules was measured with an activated partial thromboplastin time clotting assay. Results are set forth in Table II.

TABLE II

| Protein C | Anticoagulant Activity (units/mg) | Relative Activity |
|---|---|---|
| wild type | 325 ± 65 | 1 |
| Q313 | 577 ± 17 | 1.8 |
| LIN | 289 ± 13 | 0.9 |
| F167 | 283 ± 27 | 0.9 |
| FLIN | 313 ± 65 | 1 |
| FLIN-Q313 | 552 ± 37 | 1.7 |

EXAMPLE 3

Rates of Activation

Activation rates were determined using human thrombin (10 nM) in a reaction mix containing 20 mM Tris, pH 7.4, 0.15M NaCl, 0.1 mg/ml BSA and 3mM $CaCl_2$. Purified protein C, both wild type and derivatives, were at a concentration of from 0.81 to 1.61 uM in the activation reaction. Activation rates were determined by removing aliquots from the activation reaction mix at various time points to a 96-well plate and, following the addition of the chromogenic substrate (S-2366) to a final concentration of 0.75 mM, the amidolytic activity was measured as the change in absorbance units/minute at 405 nM in a ThermoMax kinetic micro-titer plate reader (Molecular Devices). Rates were determined by converting change in OD/minute to amount of activated protein C generated, using the specific activities determined for each protein, and plotting versus activation time. The amount of activated protein C generated was less than 10% of the total starting material in all experiments. The results are set forth in Table III.

TABLE III

| Protein C | Rate of Activation by Thrombin (ng/min) | Relative Rates of Activation |
|---|---|---|
| wild type | 0.53 ± 0.1 | 1 |
| Q329 | 0.23[a] | 0.4 |
| Q313 | 1.1 ± 0.2 | 2 |
| Q3Q9 | 1.62[a] | 3.3 |
| LIN | 2.2 ± 0.4 | 4 |
| F167 | 6.3 ± 1.0 | 12 |
| FLIN | 15.9 ± 4.0 | 30 |
| FLIN-Q313 | 32.3 ± 6.4 | 61 |
| FLIN-Q3Q9 | 45.0[a] | 84 |

[a]Rates with no standard deviation are from studies where n = 2?

Relative rates of activation were also determined with the same assay system using thrombin and thrombomodulin. The thrombomodulin molecule used was the soluable human thrombomodulin of Parkinson et.al., supra. The results are set forth in Table IV.

TABLE IV

| Protein C | Relative Rates of Activation by Thrombin and Thrombomodulin |
|---|---|
| wild type | 1[a] |
| Q313 | 2.6 ± 0.6 |
| LIN | 2.1 ± 0.2 |
| F167 | 3.5 ± 0.8 |
| FLIN | 2.7[a] |
| FLIN-Q313 | 9.2 ± 1.0 |

[a]Rates with no standard deviation are from studies where n = 2

EXAMPLE 4

Anticoagulant Activity in Clotting Human Plasma

Wild type human protein C and derivative FLIN-Q 313 were added to human plasma at a concentration of 20 nM, along with Helena standard APTT reagent, and incubated for 5 minutes at 37 degrees C. Clotting of the plasma was initiated by the addition of $CaCl_2$ to a final concentration of 8 mM, and the clotting times were measured. In concurrent experiments, monoclonal antibody capable of neutralizing activated protein C activity was added to control plasma and plasma containing the zymogen wild type protein C or FLIN-Q313. The results are set forth in Table V.

TABLE V

| Protein C | Clotting Time (sec) +Ab | Clotting Time (sec) −Ab |
|---|---|---|
| None (control) | 30 ± 4. | 32 ± 3 |
| wild type | 36 ± 4. | 33 ± 5 |
| FLIN-Q313 | 35 ± 4. | 75 ± 5 |

The level of clotting activity induced in the clotting plasma was determined as a function of the concentration of the wild type human protein C and the FLIN-Q313 derivative and the data was expressed as the prolongation of the clotting time. Basal clotting times in the assay were from 27 to 33 seconds. The results are set forth in Table VI.

TABLE VI

| Protein C | Dosage (nM) | Prolongation of Clotting Time (seconds) |
|---|---|---|
| wild type | 8 | 0 ± 3 |
| FLIN-Q313 | 8 | 20 ± 6 |
| wild type | 16 | 0 ± 5 |
| FLIN-Q313 | 16 | 37 ± 6 |
| wild type | 32 | 0 ± 5 |
| FLIN-Q313 | 32 | 77 ± 6 |
| wild type | 64 | 0 ± 5 |
| FLIN-Q313 | 64 | 235 ± 6 |

EXAMPLE 5

Determination of Relative Half-Lives

The inhibition of human protein C in plasma was determined by incubating normal human plasma (citrated) with 100 nM activated human protein C, activated FLIN-Q313 or zymogen (non-activated) FLIN-Q313. The plasma concentration was 90% (v/v) in the final reaction with the remaining volume consisting of buffer containing 3 mM $CaCl_2$, 150 mM NaCl, 20 mM Tris, pH 7.4 and 1 mg/ml BSA. At selected times, aliquots were removed and activated protein C activity was determined by amidolytic activity using S-2366 at a final concentration of 1 mM or by the activated partial thromboplastin time. The level of clot-activated activity of FLIN-Q313 was determined as described in Example 4. Activated protein C and activated FLIN-Q313 both displayed a greater than 50% loss in activity after about 25 minutes whereas zymogen FLIN-Q313 still maintained at least 80% activity after 45 minutes.

We claim:

1. A human protein C derivative selected from the group consisting of Q3Q9, FLIN-Q313 and FLIN-Q3Q9.

2. The human protein C derivative of claim 1 that is Q3Q9.

3. The human protein C derivative of claim 1 that is FLIN-Q313.

4. The human protein C derivative of claim 1 that is FLIN-Q3Q9.

5. A recombinant DNA molecule encoding a human protein C derivative of claim 1.

6. The recombinant DNA molecule of claim 5 that encodes the protein C derivative Q3Q9.

7. The recombinant DNA molecule of claim 5 that encodes the protein C derivative FLIN-Q313.

8. The recombinant DNA molecule of claim 5 that encodes the protein C derivative FLIN-Q3Q9.

9. The recombinant DNA molecule of claim 5 that is a plasmid.

10. The recombinant DNA molecule of claim 9 that is plasmid pGT-h-Q3Q9.

11. The recombinant DNA molecule of claim 9 that is plasmid pGT-h-FLIN-Q313.

12. The recombinant DNA molecule of claim 9 that is plasmid pGT-h-FLIN-Q3Q9.

13. A host cell transformed with a recombinant DNA plasmid of claim 9.

14. The host cell of claim 13 that is selected from the group consisting of a human kidney 293 cells and an *E. coli* cell.

15. The host cell of claim 14 that is human kidney 293 cells/pGT-h-Q 3Q9.

16. The host cell of claim 14 that is human kidney 293 cell/pGT-h-FLIN-Q 313.

17. The host cell of claim 14 that is human kidney 293 cell/pGT-h-FLIN-Q 3Q9.

18. The host cell of claim 14 that is *E. coil* K12 AG1/pGT-h-Q3Q9 (NRRL B-18938).

19. The host cell of claim 14 that is *E. coli* K12 AG1/pGT-h-FLIN-Q313 (NRRL B-18939).

20. The host cell of claim 14 that is *E. coli* K12 AG1/pGT-h-FLIN-Q3Q9 (NRRL B-18940).

21. A method of treating thrombotic disease which comprises administering to a patient in need thereof an effective amount of a protein C derivative selected from the group consisting of Q3Q9, FLIN-Q313 and FLIN-Q3Q9.

22. The method of claim 21 wherein the protein C derivative is Q3Q9.

23. The method of claim 21 wherein the protein C derivative is FLIN-Q313.

24. The method of claim 21 wherein the protein C derivative is FLIN-Q3Q9.

25. A pharmaceutical composition comprising, in a pharmaceutically acceptable diluent, a protein C derivative selected from the group consisting of Q3Q9, FLIN-Q313 and FLIN-Q3Q9.

26. The pharmaceutical composition of claim 25 wherein the protein C derivative is Q3Q9.

27. The pharmaceutical composition of claim 25 wherein the protein C derivative is FLIN-Q313.

28. The pharmaceutical composition of claim 25 wherein the protein C derivative is FLIN-Q3Q9.

* * * * *